United States Patent
Oyler

(10) Patent No.: US 9,765,362 B2
(45) Date of Patent: Sep. 19, 2017

(54) CLOSED-LOOP SYSTEM FOR GROWTH OF AQUATIC BIOMASS AND GASIFICATION THEREOF

(71) Applicant: James R. Oyler, Salt Lake City, UT (US)

(72) Inventor: James R. Oyler, Salt Lake City, UT (US)

(73) Assignee: Genifuel Corporation, Salt Lake City, UT (US)

( * ) Notice: Subject to any disclaimer, the term of this patent is extended or adjusted under 35 U.S.C. 154(b) by 0 days.

(21) Appl. No.: 14/135,379

(22) Filed: Dec. 19, 2013

(65) Prior Publication Data
US 2014/0220653 A1    Aug. 7, 2014

Related U.S. Application Data

(63) Continuation of application No. 12/683,369, filed on Jan. 6, 2010, now abandoned, which is a
(Continued)

(51) Int. Cl.
*C12P 5/02* (2006.01)
*C01B 3/50* (2006.01)
(Continued)

(52) U.S. Cl.
CPC ............ *C12P 5/023* (2013.01); *C01B 3/50* (2013.01); *C10L 3/06* (2013.01); *C10L 3/08* (2013.01);
(Continued)

(58) Field of Classification Search
CPC ........... Y02E 50/00; Y02E 50/10; C12P 5/023
See application file for complete search history.

(56) References Cited

U.S. PATENT DOCUMENTS 6,477,841 B1 * 11/2002 Yantovsky .................. 60/641.8
2007/0048859 A1   3/2007   Sears
(Continued)

FOREIGN PATENT DOCUMENTS

| AU | 2009/266842 A1 | 1/2010 |
| AU | 2009/266842 B2 | 1/2010 |

(Continued)

OTHER PUBLICATIONS

Minowa et al. A novel microalgal sysem for energy production with nitrogen cycling., Fuel (1999), vol. 78, pp. 1213-1215.*
(Continued)

*Primary Examiner* — Alexander Kim
(74) *Attorney, Agent, or Firm* — Thorpe North & Western, LLP; David W. Osborne

(57) ABSTRACT

Processes, systems, and methods for producing combustible gas from wet biomass are provided. In one aspect, for example, a process for generating a combustible gas from a wet biomass in a closed system is provided. Such a process may include growing a wet biomass in a growth chamber, moving at least a portion of the wet biomass to a reactor, heating the portion of the wet biomass under high pressure in the reactor to gasify the wet biomass into a total gas component, separating the gasified component into a liquid component, a non-combustible gas component, and a combustible gas component, and introducing the liquid component and non-combustible gas component containing carbon dioxide into the growth chamber to stimulate new wet biomass growth.

21 Claims, 1 Drawing Sheet

Related U.S. Application Data continuation-in-part of application No. 12/469,214, filed on May 20, 2009, now abandoned.

(60) Provisional application No. 61/078,235, filed on Jul. 3, 2008.

(51) Int. Cl.
| | | |
|---|---|---|
| *C01B 3/06* | (2006.01) | |
| *C10L 3/06* | (2006.01) | |
| *C10L 3/08* | (2006.01) | |
| *C10L 5/44* | (2006.01) | |
| *C12N 1/12* | (2006.01) | |
| *C12P 3/00* | (2006.01) | |

(52) U.S. Cl.
CPC .............. *C10L 5/44* (2013.01); *C12N 1/12* (2013.01); *C12P 3/00* (2013.01); *C01B 2203/0465* (2013.01); *C01B 2203/0475* (2013.01); *C10J 2300/0916* (2013.01); *C10J 2300/0986* (2013.01); *C10J 2300/1681* (2013.01); *Y02E 50/10* (2013.01); *Y02E 50/30* (2013.01); *Y02E 50/343* (2013.01)

(56) References Cited

U.S. PATENT DOCUMENTS

| | | | |
|---|---|---|---|
| 2008/0182298 A1* | 7/2008 | Day | 435/72 |
| 2010/0003717 A1 | 1/2010 | Oyler | |
| 2010/0173375 A1 | 7/2010 | Oyler | |

FOREIGN PATENT DOCUMENTS

| | | |
|---|---|---|
| AU | 2013/3205830 A1 | 5/2013 |
| JP | 2000-152799 | 6/2000 |
| JP | 2003-088838 | 3/2003 |
| JP | 2004-113087 | 4/2004 |
| WO | WO 2010/003087 | 1/2010 |

OTHER PUBLICATIONS

Gao et al., Use of macroalgae for marine biomass production and CO2 remediation: a review., Journal of Applied Phycology (1994), vol. 6, pp. 45-60.*

Aresta et al.; Utilization of macro-algae for enhanced Co2 fixation and biofuels production: Development of a computing software for LCA study; Fuel Processing Technology; 2005; pp. 1679-1693; vol. 86; Elsevier.

Chiras; Environmental Science; 2010; p. 69; Eighth Edition; Jones and Bartlett Publishers, LLC.

Elliott et al.; Chemical Processing in High-Pressure Aqueous Environments: Low-Temperature Catalytic Gasification; Chemical Engineering Research and Design; Jul. 1996; pp. 563-566; vol. 74; Institution of Chemical Engineers.

Elliott et al.; Chemical Processing in High-Pressure Aqueous Environments. 7. Process Development for Catalytic Gasification of Wet Biomass Feedstocks; Industrial & Engineering Chemistry Research; Mar. 25, 2004; pp. 1999-2004; vol. 43; American Chemical Society.

Hosoda et al.; Elimination of Environmental Impact Loads from Processed Efflux; Oceans; 2004; pp. 688-693; vol. 2; IEEE.

Huber et al.; Synthesis of Transportation Fuels from Biomass: Chemicals, Catalysts and Engineering; Chemical Review; Jun. 27, 2006; 55 pages; American Chemical Society.

Kosaric et al.; Liquid and gaseous fuels from biotechnology: challenge and opportunities; FEMS Microbiology Reviews; Feb. 1995; pp. 111-142; Federation of European Microbiological Societies/Elsevier.

Lee et al.; High-Density Algal Photobioreactors Using Light-Emitting Diodes; Biotechnology and Bioengineering; Nov. 20, 1994; pp. 1161-1167; vol. 44; John Wiley & Sons, Inc.

Melis et al.; Hydrogen Production. Green Algae as a Source of Energy; Plant Physiology; Nov. 2001; pp. 740-748; vol. 127; American Society of Plant Biologists.

Sawayama et al.; Possibility of renewable energy production and CO2 mitigation by thermochemical liquefaction of microalgae; Biomass & Bioenergy; 1999; pp. 33-39; vol. 17; Pergamon.

Valderrma; Bacterial hydrocarbon biosynthesis revisited; Studies in Surface Science and Catalysis, Chapter 13; 2004; pp. 373-384; vol. 151; Elsevier B.V.

Vermeij; Nature, an Economic History; 2004; p. 165; Princeton University Press.

Whittington; Biodiesel Production and Use by Farmers, Is it Worth Considering?; 24 pages; Jun. 2006; Department of Agriculture and Food, Government of Western Australia.

PCT Application PCT/US2009/049564; filed Jul. 2, 2009; Genifuel Corporation et al.; International Search Report mailed Mar. 16, 2010.

U.S. Appl. No. 12/469,214, filed May 20, 2009; James R. Oyler; office action dated Jul. 6, 2013.

U.S. Appl. No. 12/469,214, filed May 20, 2009; James R. Oyler; office action issued May 18, 2012.

U.S. Appl. No. 12/469,214, filed May 20, 2009; James R. Oyler; office action issued Dec. 23, 2011.

U.S. Appl. No. 12/683,369, filed Jan. 6, 2010; James R. Oyler; office action dated Sep. 19, 2013.

U.S. Appl. No. 12/683,369, filed Jan. 6, 2010; James R. Oyler; office action dated Apr. 15, 2013.

* cited by examiner

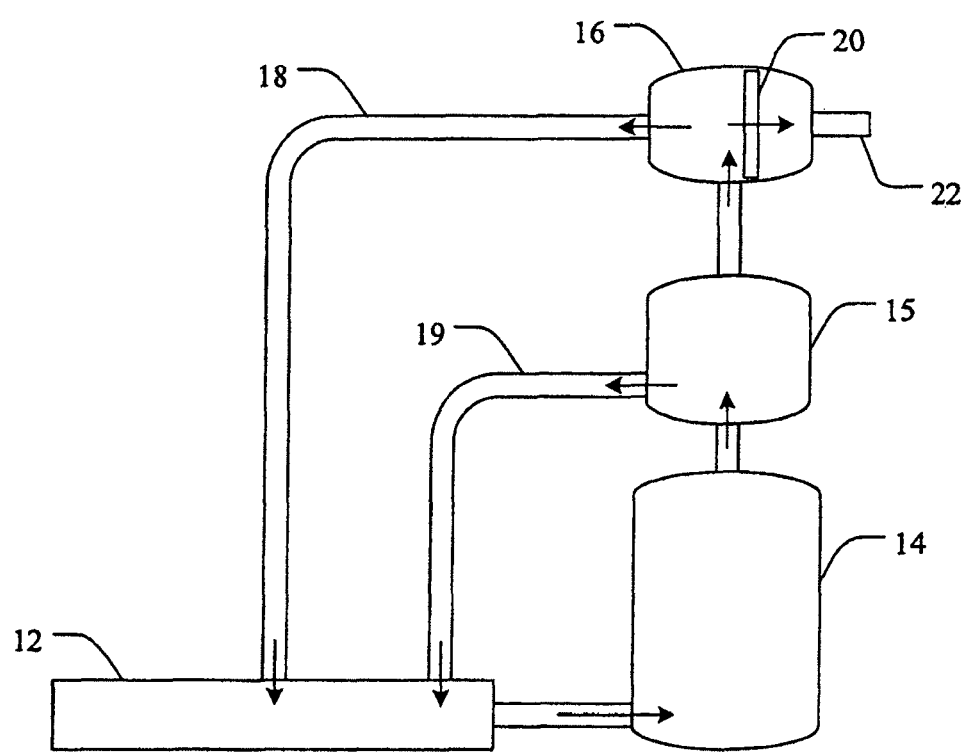

CLOSED-LOOP SYSTEM FOR GROWTH OF AQUATIC BIOMASS AND GASIFICATION THEREOF

PRIORITY DATA

This application is a continuation of U.S. patent application Ser. No. 12/683,369, filed Jan. 6, 2010, which is a continuation-in-part of U.S. patent application Ser. No. 12/469,214, filed on May 20, 2009, which claims the benefit of U.S. Provisional Patent Application Ser. No. 61/078,235, filed on Jul. 3, 2008, each of which is incorporated herein by reference.

GOVERNMENT INTEREST

This invention was made with government support under Grant Number DE-EE0003046 awarded by the Department of Energy. The Government has certain rights to this invention.

FIELD OF THE INVENTION

The present invention relates to the growth and gasification of a biomass. Accordingly, the present invention involves the biological, chemical, thermochemical, catalytic gasification, biofuels, and algacultural fields.

BACKGROUND OF THE INVENTION

In the field of biofuels production, it is desirable to efficiently convert biomass into usable fuels. Such biomass may consist of forest products or waste, terrestrial plants or crop wastes, or aquatic organisms. Fuel energy is available in such biomass because photosynthetic plants convert solar energy to stored carbohydrates, lipids, and proteins, which can then be burned directly or converted to fuels in other forms.

Various previous methods have been described for processing biomass into fuels using elevated temperature, pressure, catalyst, or all three. The reaction process can be operated under various conditions to yield various combustible gases, such as syngas (primarily carbon monoxide and hydrogen) or synthetic natural gas or SNG (primarily methane). Under still different conditions the product may be a liquid hydrocarbon.

In general, these processes use a dry feedstock. If, however, it is desired to use a feedstock with substantial water content, such as an aquatic biomass, then the process variables are different. For wet feedstocks, the pressure and temperature can often be selected to achieve acceptable yields of gas. In some cases, the necessary pressure and temperature can be lowered by the use of a catalyst. Various systems for the catalytic processing of wet biomass at reduced temperature and pressure have been previously described.

In the case of catalytic conversion of wet biomass, the fuel part of the gas is mostly methane, with a smaller amount of hydrogen and higher hydrocarbons. This mixture might be called "renewable natural gas" because the composition is essentially the same as commercially-delivered fossil natural gas. The remainder of the gas produced is typically non-combustible.

SUMMARY OF THE INVENTION

The present invention provides processes, methods, and systems for converting wet biomass into combustible gases and non-combustible gases, and returning the non-combustible portion to the growth chamber to grow new biomass. In one aspect, for example, a process for gasifying a wet biomass in a closed system is provided. Such a process may include growing a wet biomass in a growth chamber, moving at least a portion of the wet biomass to a reactor, heating the portion of the wet biomass under pressure in the reactor to gasify the wet biomass into a gas component, condensing at least portions of the gas component into a liquid, separating the remaining gas component into a non-combustible gas component and a combustible gas component, and introducing the non-combustible gas component containing carbon dioxide, and the condensed liquid, back into the growth chamber to stimulate new biomass growth. In some aspects of the invention, the step of condensing at least portions of the gas component into a liquid may include condensing most or substantially all of the non-combustible gas included in the gas component. In such an embodiment, the remaining gas component after the condensation step may be substantially combustible gas and thus the step of separating the non-combustible gas component from the combustible gas component can be substantially eliminated or eliminated completely as a separate step. Further, in such embodiment, the non-combustible gas component containing the carbon dioxide would be substantially combined with the condensed liquid at the time of introduction back into the growth chamber.

A variety of combustible gases can be generated and isolated from the gasified component according to aspects of the present invention. The species of combustible gases can be individually separated from the gasified component or they can be separated simultaneously, depending on the nature of the gas separation system. Additionally, a gas separator may isolate the combustible gases from the gasified component, or the gas separator may isolate the non-combustible gas from the gasified component. As such, in one aspect the combustible gas component can include methane. In another aspect the combustible gas component can include hydrogen. In a further aspect, the non-combustible gas component is carbon dioxide. It should be noted that the non-combustible gas can be returned to the growth chamber separately as a gas or combined with a liquid component. When combined with a liquid component, the non-combustible gases may be dissolved or combined in a liquid, including the condensate formed by the condensation step of the present methods or alternatively a liquid newly introduced into the system, for reintroduction into the growth chambers. For example, in one aspect a non-combustible gas component such as carbon dioxide can be dissolved in water, and the water containing the dissolved carbon dioxide can be introduced into the growth chamber. The closed systems according to aspects of the present invention are intended to allow the recycling of nutrients and elements derived from the gasification process back into the growth of subsequent biomass. As such, in one aspect a nutrient derived from the gasified biomass is introduced into the growth chamber to stimulate wet biomass growth. Although numerous nutrients are contemplated that would be useful for recycling, in one aspect the nutrient is ammonia. In another aspect the nutrient is an element including a member selected from the group consisting of nitrogen (N), phosphorus (P), potassium (K), calcium (Ca), magnesium (Mg), sodium (Na), sulfur (S), iron (Fe), molybdenum (Mo), silicon (Si), zinc (Zn), boron (B), cobalt (Co), copper (Cu), aluminum (Al), chlorine (Cl), and combinations thereof. Furthermore, the nutrient can be introduced into the growth chamber in a variety of forms. Nutrients can be isolated individually or in nutrient subgroups from the gasification products or they may be introduced into the growth chamber in toto. In one aspect, the nutrient can be introduced into the growth chamber as a liquid. In another aspect, the nutrients may be separated in a preprocessing step attached to the gasifier and subsequently recaptured to be returned to the growth chamber.

It should be noted that any wet biomass capable of gasification should be considered to be within the scope of the present invention. In one aspect, however, the wet biomass can include algae. Non-limiting examples of algae can include a genus of alga such as *Cladophora, Ulva*, or a combination thereof. In another aspect, the wet biomass can include cyanobacteria. Non-limiting examples of cyanobacteria can include a genus such as *Planktothrix, Oscillatoria, Nostoc, Nodularia*, or combinations thereof. In another aspect, the wet biomas can include diatoms. Non-limiting examples of diatoms include a genus such as *Navicula, Fragilaria, Nitzschia, Chaetoceros*, or combinations thereof. In another aspect, the wet biomass can include aquatic plants other than algae. Non-limiting examples include *Eichhornia* (water hyacinth) and *Pistia* (water lettuce). A wide variety of aquatic plants can be used. Additionally, the wet biomass can include algae, cyanobacteria, diatoms, other water plants, or a mixture of several or all of these.

The present invention additionally provides systems for generating combustible gas from a wet biomass. In one aspect, for example, a closed system for growing a wet biomass and converting said wet biomass into a gasification product containing methane is provided. Such a closed system can include a growth chamber for growing a wet biomass, a reactor operatively coupled to the growth chamber, where the reactor is configured to gasify the wet biomass into a gasified component, a condenser operatively coupled to the reactor, an optional gas separator operatively coupled to the reactor, wherein the gas separator can optionally be configured to separate the gasified component into a combustible gas component and a non-combustible gas component, and a recycling system configured to introduce at least a portion of the non-combustible gas component and the condensed liquid into the growth chamber to stimulate wet biomass growth. In another aspect, the system may further include a combustible gas extraction system configured to remove combustible gas from the closed system. In alternative embodiments, the system may omit the gas separator when the method specified substantially condenses or dissolves the non-combustible gas component using the condenser to separate it from the gasified component. However, when using such methods, the gas separator can optionally remain as part of the system and may either be bypassed or inoperative, or may still be used to separate the various combustible gas constituents of the combustible gas component, or any remaining or left over non-combustible gas which did not condense out during the condensation step.

In yet another aspect of the present invention, a method of minimizing external nutrient input in a process for producing a gasification product from a wet biomass is provided. Such a method may include growing a wet biomass, extracting a combustible gas from the wet biomass, and utilizing non-combustible nutrients extracted from the wet biomass for further wet biomass growth, where growing, extracting, and introducing occur in a closed system.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by the practice of the invention.

BRIEF DESCRIPTION OF THE DRAWINGS

FIG. 1 shows a schematic view of a closed-loop system for gasification of wet biomass with resource recovery.

DETAILED DESCRIPTION OF THE INVENTION

Definitions

In describing and claiming the present invention, the following terminology will be used in accordance with the definitions set forth below.

The singular forms "a," "an," and "the" include plural referents unless the context clearly dictates otherwise. Thus, for example, reference to "an alga" includes reference to one or more of such algae, and reference to "the cover" includes reference to one or more of such covers.

As used herein, "reaction" is intended to cover single step and multi-step reactions which can be direct reactions of reactants to products or may include one or more intermediate species which can be either stable or transient.

As used herein, "reactor" refers to any vessel configured to contain materials used in a process, and that can provide a proper environment for the process.

As used herein, the term "biomass" refers to various carbon-containing materials resulting from growth of photosynthetic aquatic species, but may include material from other growing organisms.

As used herein, the term "closed system" is used to refer to a system that functions with a minimal amount of added nutrient. As such, the photosynthetic aquatic systems described herein are considered to be closed systems even though sunlight, water, additional inoculations of organisms, and small amounts of nutrients to make up for nutrient loss during processing are added.

As used herein, the term "gasification product" refers to a mixture of primarily methane, with smaller amounts of hydrogen, and trace amounts of other hydrocarbons. It is understood that the initial gasification process also produces carbon dioxide, which may be removed to leave only combustible gases in the remaining product. Such removal may be accomplished by a variety of mechanisms, including condensation of non-combustible gases out of the initial gasification process by a condenser which may also condense a liquid component, or by a subsequent gas separation step performed using a gas separator.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually.

This same principle applies to ranges reciting only one numerical value as a minimum or a maximum. Furthermore, such an interpretation should apply regardless of the breadth of the range or the characteristics being described.

The Invention

The inventor has discovered a novel and efficient method and system for the production of combustible gases through the gasification of a wet biomass. The efficiency of the method and system is enhanced, at least in part, due to the recapture of carbon dioxide and the recovery of other elements remaining following gasification of the biomass. The use of recaptured carbon dioxide is thus best applied if the growing biomass is constrained in an environment where the gas may be introduced to the photosynthetic organisms without being lost. These conditions exist naturally in the aqueous conditions of growing aquatic biomass, especially if the growth structure is covered. Similarly, the recycling of the nutrient-rich remainder liquid is greatly simplified by adding it to the aqueous growth medium of aquatic biomass with or without the need for further processing. In essence, what the present invention accomplishes is to create a closed-loop system.

Processes utilized to convert biomass into usable energy are often not economically feasible due to nutrient costs associated with growing biomass. (In this discussion, hydrogen, carbon, and oxygen are considered the basis of biomass rather than nutrients. These elements are obtained primarily from water and carbon dioxide during photosynthesis). Rapid plant growth requires substantial inputs of nitrogen, phosphorus, and potassium. In addition, biomass contains many other elements or "essential elements" assimilated in normal organic growth. In approximate order of concentration, and depending on the biomass, essential elements may include nitrogen (N), phosphorus (P), potassium (K), calcium (Ca), magnesium (Mg), sodium (Na), sulfur (S), silicon (Si), iron (Fe), molybdenum (Mo), zinc (Zn), boron (B), cobalt (Co), copper (Cu), chlorine (Cl) and other elements in trace amounts. All of these elements can be important for growth, and are generally expensive in the quantities needed, and thus can substantially affect the economics of growing biomass for fuel production.

The present invention addresses the cost of nutrients by recapturing the products of gasification, other than the desired fuel, and feeding them back into the growth medium of the biomass to accelerate growth for the next cycle. Thus, in the present invention biomass is converted to gas by direct gasification, and, other than the desired fuel, products of the gasification are recycled back into the growth medium. This "closed loop" system arises because, after fuel is extracted from the biomass, the nutrients left behind are returned to the growing medium to support more biomass growth, starting the cycle over again.

While there may be losses in the recycling of nutrients, the feedback process substantially improves the economics of the overall fuel production process. In a more specific aspect, combustible gas can be generated from a wet biomass in a closed system by growing a wet biomass in the closed system, gasifying the biomass with heat and pressure, condensing a liquid component from the total gas produced, separating the remaining gas component into a non-combustible gas component and a combustible gas component, and introducing the liquid component and the non-combustible gas component containing carbon dioxide back into the growth medium to stimulate wet biomass growth. The combustible gas component can then be separated into individual gases or used in toto as a fuel source.

In particular, by control of the conditions during gasification and separation, nitrogen is converted to ammonia, carbon dioxide is separated from the combustible component, and other elements condense in a liquid phase as the reaction products are cooled. In one aspect, the carbon dioxide remains dissolved, or combined with, the liquid remainder containing the ammonia and trace elements. This mixture of dissolved carbon dioxide and nutrients is then fed back into the growth medium of the biomass to accelerate growth. It should be noted that nutrients may be fed back into the growth medium in any physical form and that some nutrients may need further processing before re-introduction to the growth medium. For example, in one aspect the carbon dioxide may be fed back as a gas. In another aspect, a liquid infused with carbon dioxide may be fed back into the growth medium. Similarly, in one aspect trace elements may be fed back into the growth medium in a gaseous or semi-gaseous form such as a wet vapor, or as a liquid. In another aspect certain elements may receive special treatment to most efficiently capture them for recycling. For example, phosphorus and other nutrients or elements may be removed either before or after the biomass is gasified, and subjected to further processing before being added to the overall nutrient mix for recycling to the growth chamber.

As previously mentioned, in some aspects, nutrients or various elements, such as phosphorous can be removed from the harvested biomass in a preprocessing step prior to gasification. Such a preprocessing step can be applied as necessary in order to retrieve the specific elements sought for recapture. For example, precipitation, filtering, settling, centrifuging, or various other forms of physical or chemical extraction can be applied to retrieve specific elements or nutrients. Once recaptured, the nutrients or elements may then be combined with the condensed liquid from the condensing step of the process following gasification for reintroduction into the growth chamber. Alternatively, the nutrients or elements may be separately reintroduced into the growth chamber to further stimulate new biomass growth.

Algae, cyanobacteria, diatoms, water hyacinths and water lettuce are non-limiting examples of biomass organisms in the methods according to aspects of the present invention because the growth rate of these organisms can be higher than other organisms. However, other aquatic plants may be used, regardless of specific growth rate. Cyanobacteria are sometimes referred to as blue-green algae, but are not actually eukaryotic algae but rather prokaryotic organisms. The choice of a specific organism or mixture of organisms, to use can be based on various growth and production considerations. As has been described, wet biomass can be produced from algae, cyanobacteria, diatoms and other aquatic plants, or a mixture of these.

In some prior attempts at the production of biofuels, significant effort has been given to growing algae species that produce a high content of either lipid or starch. Lipids and starches can be extracted to create fuels. For gasification, such content is not detrimental, but achieving a high starch or lipid content is generally not useful when the entire biomass is gasified. The primary objective for gasification is to achieve a high growth rate and biomass production, since all the biomass content will be reduced to simple molecules by the gasification conditions. Achieving high biomass growth rates can often be incompatible with high production of oil and/or starch, because when the organism is storing energy in the form of oil or starch, growth rates are generally reduced, thus defeating the goal of highest mass production. However, when algae are grown to produce lipids or starches, the extraction of these materials will leave substantial portions of the biomass as "husks" or "algae bottoms". Such remainder material can be used as the biomass feedstock for the gasification process described herein. Moreover, it is to be understood that the entire aquatic plant or species may not be used regardless of the particular type and parts only of the aquatic plant or species may be used as with the algae remainder recited above.

Once the wet biomass has grown to a sufficient quantity, at least a portion of such a biomass can be transported into a gasification reactor. Subsequently, the wet biomass is substantially reduced to a gasified form under heat and pressure. In some embodiments, a catalyst may be present and used to lower the pressure and/or temperature required to achieve the desired gasification. The equations describing separate portions of the reaction in simple form are shown in Equations I-III:

$$C_6H_{10}O_5 + H_2O \rightarrow 6CO + 6H_2 \text{ (steam reforming)} \qquad \text{I}$$

$$CO + 3H_2 \rightarrow CH_4 + H_2O \text{ (methanation)} \qquad \text{II}$$

$$CO + H_2O \rightarrow CO_2 + H_2 \text{ (water-gas shift)} \qquad \text{III}$$

The overall reaction is shown in Equation IV:

$$C_6H_{10}O_5 + H_2O \rightarrow 3CH_4 + 3CO_2 \qquad \text{IV}$$

Though the composition of the gasification product will vary somewhat depending on the reactor conditions and the physical makeup of the wet biomass, generally the gas produced will be approximately 62% methane, 35% carbon dioxide, 2% hydrogen, and 0.5% ethane by volume. More than 99% of the organic carbon is thus converted. Further details regarding the gasification reaction can be found in "Chemical Processing in High-Pressure Aqueous Environments Low-Temperature Catalytic Gasification," Trans IChemE, Vol 74, Part A, July 1996, which is incorporated herein by reference.

The reactor can function at a range of temperatures and pressures, depending on the characteristics of the wet biomass and the design of the gasification system. In one aspect, for example, the reactor can be operated at a temperature range of from about 350° C. to about 400° C. In other aspects, the temperature may be below 350° C. or above 400° C., for example from about 400° C. to about 500° C. or higher when so required to achieve a desired gasification product or from 350° C. to 250° C. or lower to achieve yet a different gasification product. Furthermore, in one aspect the reactor can be operated at a pressure range of from about 18 MPa to about 25 MPa. In other aspects the pressure range can extend up to or above 40 MPa or down to or below 15 MPa, again as required to achieve a desired gasification product.

Additionally, a catalyst material can be optionally utilized in the reactor to facilitate the gasification of the wet biomass. Although any catalyst material that facilitates such reaction may be considered to be within the present scope, specific examples can include nickel, rhodium, ruthenium, and alloys and mixtures thereof.

The novel closed-loop system described herein is significantly more efficient than an open-loop system. Approximate data for the energy balance with and without recycling is shown below:

| Typical Energy Balance (MJ/kg dry equiv. biomass) | | |
|---|---|---|
| Item | No Recycling | Recycling |
| Energy Produced | 18 | 18 |
| Nutrients other than $CO_2$ | 8 | 1 |
| Cultivation & Harvesting | 4 | 4 |
| Gasification | 2 | 2 |
| $CO_2$ Separation | 0 | 1 |
| $CO_2$ Supply | 2 | 0 |
| Net Energy | 2 | 10 |

Accordingly, using the closed-loop system with nutrient recovery substantially increases the net energy derived from the system.

As part of the closed loop, the present invention also provides systems for generating combustible gas from a wet biomass. As is shown in FIG. 1, a closed system for growing a wet biomass and converting the wet biomass into a gasification product can include a growth chamber 12 for growing a wet biomass, a reactor 14 operatively coupled to the growth chamber 12, a liquid condenser 15 operatively coupled to the reactor, a gas separator 16 operatively coupled to the reactor 14, and a recycling system 18 operatively coupled to the gas separator 16 and the growth chamber 12. The system may further include a liquid recycling system 19 operatively coupled to the liquid condenser 15 and the growth chamber 12. It should be noted that in some aspects condensed liquid recycling can occur via the recycling system 18. FIG. 1 additionally shows a separator structure 20 to separate combustible gas from non combustible gas within the gas separator 16, and an effluent 22 for removing the combustible gas from the system. As has been described, the reactor 14 is configured to gasify the wet biomass into a total gas component, the condenser 15 is configured to separate a liquid from the gas component, the gas separator 16 is configured to separate the gasified component into a combustible gas component and a non-combustible gas component, and the recycling system 18 is configured to introduce at least a portion of the non-combustible gas component into the growth chamber to stimulate wet biomass growth.

The growth chamber can be nearly any structure, arrangement, or area that provides a suitable environment for the growth of wet biomass. Examples of specific structures which can be used as a growth chamber by allowing for containment and growth of wet biomass using sunlight include without limitation, tanks, ponds, troughs, ditches, pools, pipes, tubes, canals, channels, etc., as well as other structures or arrangements recognized by those skilled in the art as suitable for such purpose. Such structures may be either open, covered, partially covered, closed, or partially closed, as long as the cover or closure allows sufficient penetration of sunlight to the biomass to permit its growth. Of course, such structure can also allow for input of water and nutrients in accordance with the process of the present invention, and also for the harvesting of the grown biomass, or a portion thereof for gasification.

In this system, the selected species grow photosynthetically, during which they capture photons from solar radiation, and use this photonic energy to convert water and carbon dioxide into organic compounds and oxygen. The organic compounds are generally proteins and carbohydrates in a wide variety of chemical structures. The chemical structures will also incorporate small amounts of other elements needed for formation of the many molecules involved in the biological processes of the organisms. Aquatic biomass can thus be grown under controlled conditions which allow water circulation, aeration to introduce carbon dioxide and remove oxygen, control of evaporation, temperature control, introduction of nutrients, and a method to recover the biomass for harvesting. Growth can take place in either open or closed ponds, which in some aspects can serve as the growth chamber. Furthermore, while the initial starter cultures for the growth medium are selected from genera similar to those mentioned herein, in practice the actual mixture of genera and species will adjust over time to optimize for growth in local conditions. The simplest method is to let the species mix adjust itself after establishing the major variables of temperature, pH, and nutrients.

Following the growth of the biomass, the aquatic biomass can be harvested for transport into the reactor. Further preparation of the biomass is optional, depending on the nature of the biomass and the associated growing conditions. For example, significant amounts of dirt or other contamination present in the biomass may be removed. One method for removal of such contaminants may include separation during settlement due to the fact that larger particles tend to settle faster than the biomass. The biomass may be ground or milled to reduce it to a slurry. Preheating of the biomass can be beneficial, which can be accomplished using recovered heat from the gasifier. The biomass can then be subsequently moved into the reactor. Such transportation of the biomass may be accomplished by mechanical methods capable of maintaining the pressure differential between the wet biomass supply tank and the gasifier.

In the reactor the complex organic structures of the biomass are broken down into much simpler structures. The energy-containing molecules (the combustible gas component) are removed to use as fuels, and the remainder is recycled to support the next cycle of biomass growth. The gasification reactor can have any of a variety of configurations, consistent mainly with the desired capacity, heating method, and catalyst structure. The reactor includes a system for recovering the gasified component, followed by a system for cooling to separate the fuel gas from the carbon dioxide and those components which will condense as a liquid.

The carbon dioxide can be processed either as a separate gas, or as a gas dissolved or combined in the liquid phase. In one embodiment, the carbon dioxide is effectively separated from the fuel gas by controlling the conditions at the exit of the gasifier so that the carbon dioxide remains dissolved in, or otherwise recombines with, the liquid phase as it condenses. The fuel gas, which is less soluble in water, can be separated as a gas.

If it is desired to keep the carbon dioxide as a gas at the exit of the gasifier, then one method for processing the carbon dioxide as a gas is to separate it from the fuel gas in a filter which can be in line or part of the gas separator. Such separation typically includes, by way of example without limitation, a membrane or other filtration technology, utilizing either a liquid or a polymer as the separation medium. Another method for such separation includes a water scrubbing system in which the remaining gas is bubbled through water in a column. Carbon dioxide will be absorbed in the water more readily than methane, thus separating the two gases. The water containing absorbed carbon dioxide can then be recycled to the growth chambers or ponds.

Once separated, the combustible gas component is then routed to either further processing, transportation, or combustion. The condensed remainder liquid, containing ammonia, carbon dioxide (if processed accordingly), and various trace elements, is recycled into the growth medium to facilitate the growth of further biomass. Additionally, if nutrients were removed from the biomass before the gasification step, then these nutrients may be re-introduced into the condensed liquid, either with or without additional processing, for recycling to the growth medium.

If the recovery and recycle processes were perfect, such a system would be completely closed-loop except for the introduction of water, carbon dioxide, and sunlight, the release of oxygen back into the atmosphere, and the removal of the combustible gas component for later use. Practically, however, the system will not be perfect and a certain amount of carbon, nitrogen, phosphorus, and trace elements, as well as makeup water, will need to be continuously supplied from outside the system. Nevertheless, the overall system is close enough to the ideal closed-loop system to substantially lower costs and make biofuel production economically feasible. This is particularly true of nitrogen and phosphorus, which are expensive and needed abundantly for optimal growth.

EXAMPLE

The growth structure includes a series of troughs approximately 2 m wide, 50 m long, and 40 cm deep built directly into the earth. The troughs contain approximately 30 cm of water. The troughs may be open or may be covered with a transparent material such as plastic film which is perforated to allow gas exchange. The covers reduce evaporation and improve temperature control in the water. The bottom and sides of the troughs may be either lined or unlined.

The water in the troughs is supplemented with nutrients needed for rapid growth, consisting of nitrogen, phosphorus, potassium, and various trace elements. The troughs have a means to introduce nutrients, as well as carbon dioxide either from the atmosphere or from supplemental sources such as the feedback from the gasifier.

The initial organisms grown in the troughs are algae, cyanobacteria, and diatoms. However, the mix of organisms will adjust autonomously over time to whatever genera and species are best adapted to the growing site.

The growing organisms are harvested continually by removing a portion of the biomass or by circulating the entire contents of the trough to a harvesting mechanism.

The biomass is processed further if needed to meet the conditions of the gasifier. For example, the biomass may be treated to remove non-biological solids and to grind or mill the wet material. It is then stored in feed tanks as a slurry. This slurry is pumped to a higher pressure and preheated for introduction to the gasifier.

The gasifier reactor is a series of stainless steel tubes or cylinders heated to 350° C. and maintained at 20 to 23 MPa pressure. A catalyst is present in the tubes. The biomass slurry is pumped into the tubes or cylinders and flows to the other end while being gasified. The gas stream is removed from the reactor and cooled. Cooling will condense a portion of the stream as water containing nitrogen (primarily as ammonia), potassium, and trace elements. The carbon dioxide is dissolved in the liquid. The liquid is then returned to the growth troughs.

The product gas consists essentially of methane, together with small amounts of hydrogen and higher hydrocarbons. This gas is sent for storage, combustion, insertion into gas pipelines, or subsequent processing. The troughs may be covered to contain the carbon dioxide, improved temperature control, and reduce evaporation of the water.

The recycled nutrients thus encourage rapid growth of the biomass in the troughs. If necessary, additional nutrients may be added from outside sources. During cooler weather, the liquid from the gasifier will be returned to the troughs hot enough to warm the water in the troughs. In warmer weather the return streams will be cooled further to avoid overheating in the troughs.

As the mixture of organisms in the troughs grows, the biomass is removed to repeat the cycle. In this way continuous operation of the gasifier is possible. However, storage tanks for the biomass slurry are also provided to allow downtime for the gasifier or to store feedstock to allow the gasifier to produce peak output during times of heavy fuel demand. The ability to produce gas on demand adds value to the operation.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A process for generating a combustible gas from a wet biomass, comprising:
   growing a wet biomass including an aquatic species selected from the group consisting essentially of: algae, cyanobacteria, diatoms, aquatic plants, and mixtures thereof in a growth chamber;
   moving at least a portion of the wet biomass to a reactor while a remainder of the wet biomass in the growth chamber continues to grow;
   heating the portion of the wet biomass under pressure with a catalyst in the reactor to gasify the wet biomass into a gasified component;
   separating the gasified component into a condensed liquid component, a non-combustible gas component containing carbon dioxide, and a combustible gas component; and
   introducing the non-combustible gas component containing carbon dioxide and the condensed liquid component into the growth chamber to stimulate continuation of the remainder of the wet biomass growth.

2. The process of claim 1, wherein the combustible gas component includes methane.

3. The process of claim 1, wherein the combustible gas component includes hydrogen.

4. The process of claim 1, wherein the gasified component is isolated and is removed from the reactor prior to separating the gasified component into the condensed liquid, non-combustible gas component containing carbon dioxide, and the combustible gas component.

5. The process of claim 1, further comprising harvesting and removing a nutrient or an element from the wet biomass and then introducing the nutrient or the element into the growth chamber to stimulate new biomass growth.

6. The process of claim 1, further comprising harvesting and removing a nutrient or an element from the gasified component and then introducing the nutrient or the element into the growth chamber to stimulate new biomass growth.

7. The process of claim 5, wherein the harvesting and removing of the nutrient or the element occurs during a preprocessing step prior to gasification of the wet biomass.

8. The process of claim 5, wherein the nutrient is ammonia.

9. The process of claim 5, wherein the element includes a member selected from the group consisting of nitrogen (N), potassium (K), calcium (Ca), magnesium (Mg), sodium (Na), sulfur (S), phosphorus (P), iron (Fe), and combinations thereof.

10. The process of claim 5, wherein the nutrient or the element is introduced into the growth chamber as a liquid.

11. The process of claim 1, wherein the non-combustible gas component is carbon dioxide.

12. The process of claim 11, wherein introducing the non-combustible gas component containing carbon dioxide into the growth chamber further includes:
   dissolving the carbon dioxide in water; and
   introducing the water containing the dissolved carbon dioxide into the growth chamber.

13. The process of claim 1, wherein the aquatic species is an algae.

14. The process of claim 13, wherein the algae includes a species from the order Cladophorales or Ulvales, and combinations thereof.

15. The process of claim 1, wherein the aquatic species is a cyanobacteria.

16. The process of claim 15, wherein the cyanobacteria includes a species from the order Oscillatoriales or Nostocales, and combinations thereof.

17. The process of claim 1, wherein the aquatic species is an aquatic plant.

18. The process of claim 17 wherein the aquatic plant includes species from the genus *Eichhornia* or *Pistia*.

19. The process of claim 1, wherein the aquatic species is a diatom.

20. The process of claim 19, wherein the diatom includes species from the genus *Navicula, Fragdaria, Nitzschia*, or *Chaetoceros*.

21. The process of claim 1, wherein the catalyst comprises ruthenium.

* * * * *